United States Patent
Cottrell et al.

(10) Patent No.: US 7,608,574 B2
(45) Date of Patent: Oct. 27, 2009

(54) AZEOTROPIC OR AZEOTROPIC-LIKE COMPOSITIONS OF 1,1,1-TRIFUOROETHANE AND 1-CHLORO-2,2,2-TRIFLUOROETHANE

(75) Inventors: Stephen A. Cottrell, Baton Rouge, LA (US); Hang T. Pham, Amherst, NY (US); Rajiv R. Singh, Getzville, NY (US); Hseuhsung Tung, Getzville, NY (US)

(73) Assignee: Honeywell International Inc., Morristown, NJ (US)

( * ) Notice: Subject to any disclaimer, the term of this patent is extended or adjusted under 35 U.S.C. 154(b) by 615 days.

(21) Appl. No.: 11/506,129

(22) Filed: Aug. 17, 2006

(65) Prior Publication Data

US 2008/0045432 A1 Feb. 21, 2008

(51) Int. Cl.
 *C11D 7/50* (2006.01)
(52) U.S. Cl. .................. 510/408; 252/67; 570/178
(58) Field of Classification Search .......... 510/408; 252/67; 570/178
 See application file for complete search history.

(56) References Cited

U.S. PATENT DOCUMENTS

| 5,175,379 | A |   | 12/1992 | Cremer et al. |
|---|---|---|---|---|
| 5,211,020 | A | * | 5/1993 | Taylor et al. .................. 62/630 |
| 5,211,867 | A | * | 5/1993 | Shankland et al. ............ 252/67 |
| 5,236,611 | A | * | 8/1993 | Shiflett ........................ 252/67 |
| 5,240,630 | A | * | 8/1993 | Sabahi et al. ................. 252/68 |
| 5,430,205 | A | * | 7/1995 | Cheminal et al. ........... 570/177 |
| 5,629,458 | A | * | 5/1997 | Thenappan et al. ......... 568/842 |
| 5,830,325 | A | * | 11/1998 | Mahler et al. ................. 203/56 |
| 6,047,560 | A | * | 4/2000 | Nishimura et al. ............ 62/617 |
| 6,395,941 | B1 | * | 5/2002 | Cheminal et al. ........... 570/169 |
| 7,405,333 | B1 | * | 7/2008 | Jackson ...................... 570/165 |
| 2005/0077501 | A1 | * | 4/2005 | Pham et al. .................. 252/364 |
| 2008/0045432 | A1 | * | 2/2008 | Cottrell et al. .............. 510/415 |

FOREIGN PATENT DOCUMENTS

WO    WO2005/097716    10/2005

* cited by examiner

*Primary Examiner*—Gregory E Webb
(74) *Attorney, Agent, or Firm*—Bruce Bradford

(57) ABSTRACT

Azeotropic or azeotropic-like compositions of 1,1,1-trifluoroethane (HFC-143a) and 1-chloro-2,2,2-trifluoroethane (R-133a).

33 Claims, No Drawings

AZEOTROPIC OR AZEOTROPIC-LIKE COMPOSITIONS OF 1,1,1-TRIFUOROETHANE AND 1-CHLORO-2,2,2-TRIFLUOROETHANE

FIELD OF THE INVENTION

This invention relates to compositions of 1,1,1-trifluoroethane (HFC-143a) and more specifically to azeotropic and azeotropic-like compositions of 1,1,1-trifluoroethane and 1-chloro-2,2,2-trifluoroethane (R-133a).

BACKGROUND TO THE INVENTION

A number of processes for the production of 1,1,1-trifluoroethane (HFC-143a) are known. However, the products of these processes contain reaction by-products, among which is 1-chloro-2,2,2-trifluoroethane (R-133a). It is highly desirable to be able to remove such reaction by-products in order to achieve purer 1,1,1-trifluoroethane or a 1,1,1-trifluoroethane compositions having a boiling point within a relatively small range.

Unfortunately, as is known to those in the relevant art, the combination of two or more constituents forming an HFC/non-HFC mixture often results in compositions wherein relatively small changes in the relative amounts of the constituents results in relatively large changes in the boiling point and vapor pressure of the mixture. For example, the boiling point and vapor pressure characteristics of many typical HFC/non-HFC mixtures can be predicted using Regular Solution mathematical models as described in Praunitz, Lichtenthaler, Azevedo "Molecular Thermodynamics in Fluid-Phase Equilibria", pp 179-190 (second edition), Prentice-Hall, Inc., incorporated herein by reference thereto. As illustrated by Prausnitz et al., a plot of vapor pressure or boiling point of a regular solution versus it's constituent composition tends to have a significantly positive slope, indicating that relatively large changes in vapor pressure or boiling point occur upon relatively small changes in the constituent composition. Accordingly, mixtures having only relatively small differences in constituent amounts may still have relatively large changes in boiling points. Thus, there is a need to identify a binary azeotropic or azeotropic-like mixture of HFC-143a and R-133a so that modeling and simulation may be accomplished to identify the correct necessary separation equipment and methods to better obtain purities of final HFC-143a product.

SUMMARY OF THE INVENTION

Applicants have come to appreciate that mixtures having a relatively constant boiling point, that is, a boiling point that changes by a relatively small amount as the constituent amounts of the mixture changes, are difficult to separate. (Deleted texts as we are not focusing on spraying applications but on separation process by distillation). Unfortunately, mixtures having such relatively constant boiling point properties are not only uncommon, but also unpredictable.

The present inventors have discovered azeotropic or azeotropic-like compositions of effective amounts of 1,1,1-trifluoroethane (HFC-143a) and 1-chloro-2,2,2-trifluoroethane (R-133a). The discovery of the azeotropic or azeotropic-like compositions of HFC-143a and R-133a permits such azeotropic or azetropic-like compositions to be distilled off from a composition containing both HFC-143a and R-133a in a distillation column whereby the concentration of R-133a at the top of the column is greater than the concentration of R-133a in the bottom of the column. This distillation process has particular applicability in purifying HFC-143a when it is produced from the reaction of vinylidene chloride with HF since the azeotropic or azeotropic-like compositions of HFC-143a and R-133a can be distilled from the products of that reaction in order to purify the HFC-143a produced.

DETAILED DESCRIPTION OF THE INVENTION

In accordance with the present invention it has been discovered that there are azeotropic or azeotropic-like compositions of effective amounts of 1,1,1-trifluoroethane (HFC-143a) and 1-chloro-2,2,2-trifluoroethane (R-133a). The discovery of the azeotropic or azeotropic-like compositions of HFC-143a and R-133a permits such azeotropic or azeotropic-like compositions to be distilled off from a composition containing both HFC-143a and R-133a in a distillation column whereby the concentration of R-133a at the top of the column is greater than the concentration of R-133a in the bottom of the column. This distillation process has particular applicability in purifying HFC-143a when it is produced from the reaction of vinylidene chloride with HF since the azeotropic or azeotropic-like compositions of HFC-143a and R-133a can be distilled from the products of that reaction in order to purify the HFC-143a produced. The azeotropic or azeotropic-like composition of HFC-143a and R-133a from the top of the column can be recycled or sent back to the reactor for conversion of R-133a to HFC-143a.

It has been further discovered that HFC-143a and R-133a form azeotropic or azeotropic-like compositions having a boiling point with a relatively small range of −46.5±2° C. at atmospheric pressure (14.42 psia). In a further embodiment, the azeotropic or azeotropic-like compositions have a boiling point of from about −46.6 to about −47.2° C. In a still further embodiment, the azeotropic or azeotropic-like compositions have a boiling point of from about −46.8° C. to about −47.2° C. In a yet further embodiment the azeotropic or azeotropic-like compositions have a boiling point of from about −47° C. to about −47.2° C. In another still further embodiment, the azeotropic or azeotropic-like compositions have a boiling point of about −47.2° C.

Such azeotropic or azeotropic-like compositions generally are mixtures of HFC-143a and R-133a wherein the composition comprises, and preferably consists essentially of:

from about 70% by weight up to an amount just less than about 100% by weight of HFC-143a, and from about 30% by weight down to an amount just more than 0% by weight of R-133a, wherein the weight percentages are based on the total weight of the composition.

In a further embodiment of the invention the azeotropic or azeotropic-like compositions generally are mixtures of HFC-143a and R-133a wherein the composition comprises, and preferably consists essentially of:

from about 75% by weight up to about 99.9% by weight of HFC-143a, and from about 0.1% by weight to about 25% by weight of R-133a, wherein the weight percentages are based on the total weight of the composition. The azeotropic or azeotropic-like composition of HFC-143a and R-133a from the top of the column can be recycled or sent back to the reactor for conversion of R-133a to HFC-143a.

In a still further embodiment of the invention the azeotropic or azeotropic-like compositions generally are mixtures of HFC-143a and R-133a wherein the composition comprises, and preferably consists essentially of:

from about 90% by weight up to about 99.9% by weight of HFC-143a, and from about 0.1% by weight to about 10% by weight R-133a, wherein the weight percentages are based on the total weight of the composition. The azeotropic or azeotropic-like composition of HFC-143a and R-133a from the top of the column can be recycled or sent back to the reactor for conversion of R-133a to HFC-143a.

The inventors have also discovered that during a distillation process involving 143a and 133a mixtures, the 133a will tend to accumulate in the upper, cooler part of the column, up to the azeotropic composition, instead of the bottom, warmer part of the column. This property may be used to remove the 133a, the undesirable component, from the mixture, as the pure 143a, having a boiling point higher than of the azeotrope, will tend to accumulate in the bottom of the column, from where it can be extracted. Thus, a distillation process of this invention will comprise distilling an azeotropic or azeotropic-like HFC-143a/HCFC-133a composition and as a result of the distillation the 133a concentration on the top of the column is higher than the 133a concentration in the composition in the bottom of the column. In accordance with an embodiment of the invention the azetropic or azetropic-like compositions being distilled are azeotropic or azeotropic-like compositions of effective amounts of 1,1,1-trifluoroethane (HFC-143a) and 1-chloro-2,2,2-trifluoroethane (R-133a). It has further been discovered that HFC-143a and R-133a form azeotropic or azeotropic-like compositions being distilled may have a boiling point with a relatively small range of −46.5±2° C. at atmospheric pressure (14.42 psia). In a further embodiment, the azeotropic or azeotropic-like compositions being distilled have a boiling point of from about −46.6 to about −47.2° C. In a still further embodiment, the azeotropic or azeotropic-like compositions being distilled have a boiling point of from about −46.8° C. to about −47.2° C. In a yet further embodiment the azeotropic or azeotropic-like compositions being distilled have a boiling point of from about −47° C. to about −47.2° C. In another still further embodiment, the azeotropic or azeotropic-like compositions being distilled have a boiling point of about 47.2° C.

In the distillation process, the azeotropic or azeotropic-like compositions generally are mixtures of HFC-143a and R-133a wherein the composition comprises, and preferably consists essentially of:

from about 70% by weight up to an amount just less than about 100% by weight Of HFC-143a, and from about 30% by weight down to an amount just more than 0% by weight of R-133a, wherein the weight percentages are based on the total weight of the composition.

In a further embodiment of the invention, in the distillation process, the azeotropic or azeotropic-like compositions generally are mixtures of HFC-143a and R-133a wherein the composition comprises, and preferably consists essentially of:

from about 75% by weight up to about 99.9% by weight of HFC-143a, and from about 0.1% by weight to about 25% by weight of R-133a, wherein the weight percentages are based on the total weight of the composition.

In a still further embodiment of the invention, in the distillation process, the azeotropic or azeotropic-like compositions generally are mixtures of HFC-143a and R-133a wherein the composition comprises, and preferably consists essentially of:

from about 90% by weight up to about 99.9% by weight of HFC-143a, and from about 0.1% by weight to about 10% by weight of R-133a, wherein the weight percentages are based on the total weight of the composition.

The invention will be particularly useful when HFC-143a is produced by the reaction of vinylidene chloride with HF and the reaction product contains HFC-143 a and R-133a since the afore-mentioned distillation process may be conducted on the products of that reaction to distill off from the products of that reaction any of the azeotropic or azeotropic-like compositions as described herein before in order to purify the HFC-143a product produced.

This invention provides azeoptropic or azeoptropic-like compositions of HFC-143a and R-133a having a boiling point with a relatively small range of ±2° C. at atmospheric pressure (14.42 psia). Such azeotropic or azeotropic-like compositions generally are mixtures of HFC-143a and R-133a wherein the composition comprises, and preferably consists essentially of:

from about 70% by weight up to an amount just less than about 100% by weight of HFC-143a, and from about 30% by weight down to an amount just more than 0% by weight R-133a, wherein the weight percentages are based on the total weight of the composition. Such compositions will have a boiling point at atmospheric pressure (14.42 psia) within the relatively small range of −46.5±2° C. Preferred compositions of this invention are those consisting essentially of about 75% to about 99% by weight of HFC-143a and from about 1% to about 25% by weight of R-133a and having a boiling point at atmospheric pressure of about −46.5±2° C. More preferred compositions of this invention are those consisting essentially of about 90% to about 99% by weight of HFC-143a and from about 1% to about 10% by weight of R-133a and having a boiling point at atmospheric pressure of about −46.5±2° C.

Because the normal boiling points of pure HFC-143a and R-133a at 1 atmosphere pressure are −47° C. and 6° C., respectively, R-133a would be expected to be removed as the residue, or bottoms product, in a distillation of a HFC-143a and R-133a mixture.

A further aspect of this invention is a process for removing 1-chloro-2,2,2-trifluoroethane (R-133a) impurity from a mixture 1,1,1-trifluoroethane (HFC-143a) and R-133a impurity comprising forming an azeotropic or azeotrope-like composition of the HFC-143a and R-133a, as described herein before, and thereafter separating the azeotropic or azeotrope-like composition from the mixture.

As shown in Table 1, the binary azeotrope or azeotrope-like mixture 143a/133a was discovered when the higher boiling point 133a (−6° C.) was added to 143a (−46.5° C.). The temperature of the mixture is lower than the boiling temperature of either pure components. The azeotropic or azeotropic-like compositions of this invention are illustrated by, but not limited to, the following examples in Table 1 of compositions having a boiling point within the range of −46.5±2° C.

TABLE 1

| Wt % HFC-143a | Wt % R-133a | Boiling point at atmospheric pressure ° C. |
|---|---|---|
| 100.00 | 0.00 | −46.5 |
| 99.04 | 0.96 | −47.2 |
| 94.72 | 5.28 | −47.2 |
| 89.23 | 10.77 | −47.0 |
| 84.65 | 15.35 | −46.8 |
| 80.75 | 19.25 | −46.6 |
| 75.57 | 24.43 | −45.1 |
| 71.73 | 28.27 | −44.1 |

Having described the invention in detail by reference to the preferred embodiments and specific examples thereof, it will be apparent that modifications and variations are possible without departing from the spirit and scope of the disclosure and claims.

We claim:

1. An azeotropic or azeotropic-like composition comprising effective amounts of 1,1,1-trifluoroethane (HFC-143a) and 1-chloro-2,2,2-trifluoroethane (R-133a).

2. An azeotropic or azeotropic-like composition according to claim 1, which consists essentially of effective amounts of 1,1,1-trifluoroethane (HFC-143a) and 1-chloro-2,2,2-trifluoroethane (R-133a).

3. An azeotropic or azeotropic-like composition according to claim 1 which consists essentially of:
from about 70% up to an amount just less than about 100% by weight of HFC-143a, and
from about 30% by weight down to an amount just more than 0% by weight of R-133a,
wherein the weight percentages are based on the total weight of the composition.

4. An azeotropic or azeotropic-like composition according to claim 1 which consists essentially of:
from about 75% to about 99.9% by weight of HFC-143a, and
from about 0.1 to about 25% by weight of R-133a,
wherein the weight percentages are based on the total weight of the composition.

5. An azeotropic or azeotropic-like composition according to claim 1 which consists essentially of:
from about 90% to about 99.9% by weigh of HFC-143a, and
from about 0.1 to about 10% by weigh of R-133a,
wherein the weight percentages are based on the total weight of the composition.

6. An azeotropic or azeotropic-like composition according to claim 1 which has a boiling point of about 46.5±2° C. at an atmospheric pressure of about 14.42 psia.

7. An azeotropic or azeotropic-like composition according to claim 1 which has a boiling point of about −46.6° C. to about −47.2° C. at an atmospheric pressure of about 14.42 psia.

8. An azeotropic or azeotropic-like composition according to claim 1 which has a boiling point of about −46.8° C. to about −47.2° C. at an atmospheric pressure of about 14.42 psia.

9. An azeotropic or azeotropic-like composition according to claim 1 which has a boiling point of about −47° C. to about −47.2° C. at an atmospheric pressure of about 14.42 psia.

10. An azeotropic or azeotropic-like composition according to claim 1 which has a boiling point of about −47.2° C. at an atmospheric pressure of about 14.42 psia.

11. In a process for producing 1,1,1-trifluoroethane (HFC-143a) by the reaction of vinylidene chloride with HF, the improvement comprising purifying the 1,1,1-trifluoroethane (HFC-143a) by distilling off from the product of the reaction an azeotropic or azeotrope-like composition comprising effective amounts of 1,1,1-trifluoroethane (HFC-143a) and 1-chloro-2,2,2-trifluoroethane (R-133a).

12. The process according to claim 11 wherein the azeotropic or azeotrope-like composition distilled from the product of the reaction consists essentially of effective amounts of 1,1,1-trifluoroethane (HFC-143a) and 1-chloro-2,2,2-trifluoroethane (R-133a).

13. The process according to claim 11 wherein the azeotropic or azeotrope-like composition distilled from the product of the reaction consists essentially of: from about 70% by weight up to an amount just less than about 100% by weight of HFC-143a, and from about 30% by weight down to an amount just more than 0% by weight of R-133a, wherein the weight percentages are based on the total weight of the composition.

14. The process according to claim 11 wherein the azeotropic or azeotrope-like composition distilled from the product of the reaction consists essentially of: from about 75% to about 99.9% by weight of HFC-143a, and from about 0.1 to about 25% by weight of R-133a, wherein the weight percentages are based on the total weight of the composition.

15. The process according to claim 11 wherein the azeotropic or azeotrope-like composition distilled from the product of the reaction consists essentially of
from about 90% to about 99.9% by weight of HFC-143a, and
from about 0.1 to about 10% by weight of R-133a,
wherein the weight percentages are based on the total weight of the composition.

16. The process according to claim 11 wherein the azeotropic or azeotrope-like composition distilled from the product of the reaction has a boiling point of about 46.5±2° C. at an atmospheric pressure of about 14.42 psia.

17. The process according to claim 11 wherein the azeotropic or azeotrope-like composition distilled from the product of the reaction has a boiling point of about −46.6° C. to about −47.2° C. at an atmospheric pressure of about 14.42 psia.

18. The process according to claim 11 wherein the azeotropic or azeotrope-like composition distilled from the product of the reaction has a boiling point of about −46.8° C. to about −47.2° C. at an atmospheric pressure of about 14.42 psia.

19. The process according to claim 11 wherein the azeotropic or azeotrope-like composition distilled from the product of the reaction has a boiling point of about −47° C. to about −47.2° C. at an atmospheric pressure of about 14.42 psia.

20. The process according to claim 11 wherein the azeotropic or azeotrope-like composition distilled from the product of the reaction has a boiling point of about −47.2° C. at an atmospheric pressure of about 14.42 psia.

21. The process according to claim 11 wherein the azeotropic or azeotrope-like composition distilled from the product of the reaction is recycled back to the reactor.

22. A process for removing 1-chloro-2,2,2-trifluoroethane (R-133a) impurity from a mixture 1,1,1-trifluoroethane (HFC-143a) and R-133a impurity comprising forming an azeotropic or azeotrope-like composition of the HFC-143a and R-133a and thereafter separating the azeotropic or azeotrope-like composition from the mixture.

23. The process according to claim 22 wherein the separation is conducted by distillation.

24. The process according to claim 22 wherein the azeotropic or azeotrope like composition consists essentially of effective amounts of 1,1,1-trifluoroethane (HFC-143a) and 1-chloro-2,2,2-trifluoroethane (R-133a).

25. The process according to claim 22 wherein the azeotropic or azeotrope-like composition consists essentially of from about 70% by weight up to an amount just less than about 100% by weight of HFC-143a, and from about 30% by weight down to an amount just more than 0% by weight of R-133a, wherein the weight percentages are based on the total weight of the composition.

26. The process according to claim 22 wherein the azeotropic or azeotrope-like composition consists essentially of from about 75% to about 99.9% by weight of HFC-143a, and from about 0.1 to about 25% by weight of R-133a, wherein the weight percentages are based on the total weight of the composition.

27. The process according to claim 22 wherein the azeotropic or azeotrope-like composition consists essentially of from about 90% to about 99.9% by weight of HFC-143a, and from about 0.1 to about 10% by weight of R-133a, wherein the weight percentages are based on the total weight of the composition.

28. The process according to claim 22 wherein the azeotropic or azeotrope-like composition has a boiling point of about 46.5±2° C. at an atmospheric pressure of about 14.42 psia.

29. The process according to claim 22 wherein the azeotropic or azeotrope-like composition has a boiling point of about −46.6° C. to about −47.2° C. at an atmospheric pressure of about 14.42 psia.

30. The process according to claim 22 wherein the azeotropic or azeotrope-like composition has a boiling point of about −46.8° C. to about −47.2° C. at an atmospheric pressure of about 14.42 psia.

31. The process according to claim 22 wherein the azeotropic or azeotrope-like composition has a boiling point of about −47° C. to about −47.2° C. at an atmospheric pressure of about 14.42 psia.

32. The process according to claim 22 wherein the azeotropic or azeotrope-like composition has a boiling point of about −47.2° C. at an atmospheric pressure of about 14.42 psia.

33. A process of distilling a composition comprising HFC-143a and R133a in a distillation column wherein, as a result of the distillation, the R-133a concentration is higher at the top of the column is higher than the concentration of R-133a in the composition at the bottom of the column.

* * * * *

UNITED STATES PATENT AND TRADEMARK OFFICE
CERTIFICATE OF CORRECTION

PATENT NO. : 7,608,574 B2  Page 1 of 1
APPLICATION NO. : 11/506129
DATED : October 27, 2009
INVENTOR(S) : Cottrell et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 686 days.

Signed and Sealed this

Twelfth Day of October, 2010

David J. Kappos
*Director of the United States Patent and Trademark Office*